United States Patent [19]

Sonoyama et al.

[11] 3,998,697

[45] Dec. 21, 1976

[54] PROCESS FOR PREPARING 2-KETO-L-GULONIC ACID

[75] Inventors: Takayasu Sonoyama, Sakai; Hiroyoshi Tani, Moriguchi; Bunji Kageyama, Nagaokakyo; Kobee Kobayashi, Nishinomiya; Tahiko Honjo, Minoo; Shigeo Yagi, Takatsuki, all of Japan

[73] Assignee: Shionogi & Co., Ltd., Osaka, Japan

[22] Filed: Apr. 21, 1975

[21] Appl. No.: 569,852

[30] Foreign Application Priority Data

Sept. 20, 1974 Japan .................. 49-109314

[52] U.S. Cl. .................. 195/47; 195/111
[51] Int. Cl.² .................. C12D 1/06
[58] Field of Search .......... 195/30, 42, 47, 111, 195/112, 13

[56] References Cited

UNITED STATES PATENTS

| 2,948,659 | 8/1920 | Shoemaker | 195/47 |
| 3,907,639 | 9/1975 | Makover et al. | 195/47 |

FOREIGN PATENTS OR APPLICATIONS

| 7,238,193 | 9/1972 | Japan | 195/30 |

OTHER PUBLICATIONS

Sonoyama et al., "2–Keto–Gulonic Acid by Fermentation," *Chemical Abstracts* vol. 82, No. 15275k (1975).

*Primary Examiner*—A. Louis Monacell
*Assistant Examiner*—Thomas G. Wiseman
*Attorney, Agent, or Firm*—Stewart and Kolasch, Ltd.

[57] ABSTRACT

2-Keto-L-gulonic acid is prepared directly from D-glucose by microbial conversion utilizing mixed culturing on or mixed contacting with a medium containing D-glucose, employing at least two kind of microorganisms; 2,5-diketo-D-gluconic acid producing strains which belong to the genera of Acetobacter, Acetomonas and Gluconobacter and strains capable of converting the 2,5-diketo-D-gluconic acid into 2-keto-L-gulonic acid which belong to the general of Brevibacterium and Corynebacterium. Both the incubation of the microorganisms in a medium containing D-glucose and the direct contact of any products obtained from the cells of the microorganisms with the substrate may be used in the disclosed process. By-production of the undesired optical isomer, 2-keto-D-gluconic acid, of the intended product is effectively prevented by employing the mixed culturing or contacting because of the presence of the 2,5-diketo-D-gluconic acid producing strain or any products thereof in the medium during at least part of the entire process.

50 Claims, No Drawings

PROCESS FOR PREPARING 2-KETO-L-GULONIC ACID

BACKGROUND OF THE INVENTION

1. Field of the Invention

The present invention generally relates to the microbial production of 2-keto-L-gulonic acid. More particularly, it concerns a process of preparation wherein 2-keto-L-gulonic acid is directly obtained from D-glucose by a mixed culturing of a plurality of microorganisms in a single fermenter or by a mixed contacting of a plurality of products obtained by treating said microorganisms in a single vessel.

2. Description of the Prior Art

The 2-keto-L-gulonic acid, which is useful as an intermediate for synthesizing L-ascorbic acid, has heretofore been commercially produced by the so-called "Reichstein's method", which is well known as a technologically established process. This method, however, comprises a number of complex steps and therefore any improvement in the overall yield is very difficult to achieve if not completely impossible. Therefore, there has hitherto been a number of proposals which contemplate a reduction in the number of steps and/or an improvement in the overall yield.

For instance, a biochemical method wherein 5-keto-D-gluconic acid, an oxidized product of D-glucose, is reduced to 2-keto-L-gulonic acid, a method of direct microbial conversion of L-sorbose into 2-keto-L-gulonic acid and the like are already known in the art.

These proposed methods have at least theoretically succeeded in the reduction in the number of the steps required for the production of 2-keto-L-gulonic acid but unexceptionally failed in the actual improvement in the overall yield and the feasibility or the steady operation of the total system.

Moreover, the attendant disadvantageous abundance of the resultant by-product both in terms of kind and quantity, difficulty in the separation of the intended product from the mixture which contains the by-products, and complexity in the operation, hinder the commercialization of these processes.

SUMMARY OF THE INVENTION

It is therefore an object of the present invention to provide a novel method for preparing 2-keto-L-gulonic acid which has achieved a reduction in the number of steps required for obtaining the intended product in the prior art processes. The improvement in terms of the reduction in the number of steps is very significant because it leads to a one step pathway directed to the production of the 2-keto-L-gulonic acid from D-glucose, resulting in two steps for that of L-ascorbic acid and D-glucose.

Another object of the present invention is to provide a manner or mode of operation wherein the previously described method is performed more effectively by preventing the production of the undesired optical isomer of the intended product.

According to the present invention, there is provided a method for producing 2-keto-L-gulonic acid which comprises; contacting a microorganism strain capable of producing 2,5-diketo-D-gluconic acid from D-glucose which belongs to the genera of Acetobacter, Acetomonas and Gluconobacter or any product obtained by treating cells of said microorganism having an enzymatic activity for the same effect, and a microorganism capable of converting 2,5-diketo-D-gluconic acid into 2-keto-L-gulonic acid which belongs to the genera of Brevibacterium and Corynebacterium or any product obtained by treating cells of said microorganism having an enzymatic activity for the same effect, with a medium containing D-glucose in a manner wherein both microorganisms or products thereof coexist together in the medium during at least part of the entire process in a condition sufficient to produce and accumulate 2-keto-L-gulonic acid or any salts thereof in the medium and recovering the same from the resultant mixture.

As being apparent from the above statement, the key intermediate in the process of the present invention is 2,5-diketo-D-gluconic acid. Some of the inventors have already described a procedure wherein 2-keto-L-gulonic acid is prepared from this intermediate (U.S. Patent Application Ser. No. 452,656, filed on Mar. 19, 1974, now U.S. Pat. No. 3,922,194, which issued on Nov. 25, 1975). However, since this intermediate is relatively unstable to heat or to other treatment, utilization of a broth containing both the acid and the microorganism cells which have served for the production of the acid, without an isolation step or another treatment which may cause degradation of the acid, has been keenly desired.

Apart from this factor, pure unmixed cultures of the microorganism strains that are capable of converting 2,5-diketo-D-gluconic acid into 2-keto-L-gulonic acid have the disadvantage of by-producing the undesired optical isomer, 2-keto-D-gluconic acid, of the intended product, resulting in difficulty in the separation of the isomer from the product, though the by-production may be suppressed by mutating or modifying the strain.

The present inventors have now found the fact that the 2,5-diketo-D-gluconic acid producing strain and the 2-keto-L-gulonic acid producing strain can coexist in the same fermentation broth and that the 2,5-diketo-D-gluconic acid produced from D-glucose by the 2,5-diketo-D-gluconic acid producing strain accumulated in a crude state, can be utilized by the 2-keto-L-gulonic acid producing strain without any disadvantages, and that the aforesaid undesired optical isomer which is by-produced along with the end product by the 2-keto-L-gulonic acid producing strain is, actually, not accumulated in the broth; the by-produced 2-keto-D-gluconic acid is converted again into 2,5-diketo-D-gluconic acid by the 2,5-diketo-D-gluconic acid producing strain for the repeated utilization by the 2-keto-L-gulonic acid producing strain.

In this specification, the microorganism strain capable of producing 2,5-diketo-D-gluconic acid from D-glucose (hereinafter, called "Strain A") employed herein belongs to the genera of Acetobacter, Acetomonas and Gluconobacter, although these three genera are not specifically discriminated with respect to each other in the description of Bergey's Manual of Determinative Bacteriology (7th Ed.).

The microorganism strain capable of converting 2,5-diketo-D-gluconic acid into 2-keto-L-gulonic acid (hereinafter, called "Strain B") employed herein belongs to the genera of Brevibacterium and Corynebacterium.

In this specification and claims the expression "contacting . . . in a manner wherein both microorganisms . . . coexist together in the medium during at least part of the entire process means principally "mixed culture" wherein both microorganisms grow together in the medium although, such expression or definition is intended to include the case wherein any product obtained by treating the cells of the microorganism, for instance, resting cells, lyophilized cells, immobilized cells, ground product of the cells, or any enzyme secreted and/or extracted from the cells is employed for the process, in addition to the incubation with the microorganisms.

The "mixed culture" can be conducted by means of a variety of methods; for instance, a method wherein both kinds of microorganism strains are simultaneously inoculated in the medium at the initiation of the culture, a method wherein Strain A is inoculated first and Strain B is subsequently inoculated after a period of incubation, and a method wherein the both strains are inoculated separately in the respective media and then either one of the both is added to the other broth all at once, portionwise or continuously after some period of incubation, followed by another period of incubation.

In the process of the present invention, any suitable method may be selected for the strains to be cultured by changing the method of mixing in compliance with the properties of the individual strain to be employed.

Namely, the ratio of the amount of one of the strains to be inoculated with respect to that of the other, and the times of the inoculations, are selected and determined in view of the growth rate of the respective strains and the 2,5-diketo-D-gluconic acid producing ability and the ability for converting 2,5-diketo-D-gluconic acid into 2-keto-L-gulonic acid of the strains, and on the basis of the properties of the media to be utilized. In some cases, products obtained by treating the cells which retain an enzymatic activity, may partly be used as a substitute for either one of the growing cells.

In the followings, Strains A and B which can be employed in the method of the present invention, including those which are being preserved in a public depository (culture collection) for delivery to any one upon request such as the Institute of Fermentation Osaka, Japan (IFO), are listed for exemplification and then the taxonomical descriptions of the strains isolated from soil and deposited with the Fermentation Research Institute (a division of the agency of industrial science and technology, Japan) as FERM-Ps and with the American Type Culture Collection as ATCCs by the present inventors are made in due order in the following pages.

STRAIN A

1. *Acetomonas albosesamae* FERM-P No. 2439, ATCC No. 21998.
2. *Acetobacter melanogenum* IFO No. 3293.
3. *Gluconobacter rubiginosus* IFO No. 3244.

STRAIN B

1. *Brevibacterium ketosoreductum* ASM-1005, FERM-P No. 1905, ATCC No. 21914.
2. *Brevibacterium nov. sp.* ASM-856-4, FERM-P No. 2686, ATCC No. 31083.
3. *Brevibacterium sp.* ASM-3356-31, FERM-P No. 2685, ATCC No. 31082.
4. *Brevibacterium testaceum* IFO No. 12675.
5. *Corynebacterium sp.* ASM-3311-6, FERM-P No. 2687, ATCC No. 31081.
6. *Corynebacterium sp.* ASM-20A-77, FERM-P No. 2770, ATCC No. 31090.
7. *Corynebacterium sp.* ASM-T-13, FERM-P No. 2771, ATCC No. 31089.
8. *Corynebacterium sp.* ASM-K-106, FERM-P No. 2769, ATCC 31088.

Strain A, 1. *Acetomonas albosesamae* (Wakisaka) ATCC No. 21998

A. Observations:
 1. Shape of cells (Glucose-Yeast extract agar slant at 28° C for 3 days): Rods 0.6-0.8 by 1.2-3.5 $\mu$, with rounded ends occurring singly and in slimy masses. No pleomorphism but some filamentous form is observed.
 2. Motility (Glucose-bouillon broth and soft agar at 30° C for 24 hours): Motile with subpolar flagellum. Many of the cells lack flagellum.
 3. Spore (Glucose-Yeast extract agar slant at 28° C for 7 days): Not formed.
 4. Gram staining (Glucose-Yeast extract agar slant at 28° C for 12, 20, 36 and 72 hours): Negative.
 5. Acid-fast staining (Glucose-Yeast extract agar slant at 28° C for 72 and 360 hours): Negative.
B. Growth on various media:
 1. Agar colonies (Glucose-Yeast extract agar at 28° C for 1-3 days): Circular, convex, entire colonies of smooth surface, translucent to opaque density, grayish white in color and brittle to butyrous consistency.
 2. Agar slant (Glucose-Yeast extract agar at 28° C for 1-3 days): Moderate, filiform, brittle to butyrous structure, grayish-white color growth of dull shining surface and translucent to a little opaque optical density. No diffusible pigment is observed at early stage but slightly pale yellowish brown pigment is observed at late stage.
 3. Growth in broth (Emerson's medium at 28° C for 1-3 days): Moderate, flocculent growth on the upper layer at early stage. No pellicle formation.
 4. Bouillon gelatin stab (at 27° C for 1-30 days): Scanty growth and no liquefaction.
 5. Litmus milk: Rapid acidification with reduction of the litmus. No peptonization is observed.
C. Physiological properties (unless otherwise indicated, based on the results of the observation at 28° C for 1-7 days):
 1. Nitrite: Nitrite is produced from nitrate.
 2. Methyl-red reaction: Positive.
 3. Voges-Proskauer's reaction: Negative.
 4. Indole: Not produced.
 5. Hydrogen sulfide (lead paper method): Produced.
 6. Starch: Not hydrolyzed.
 7. Utilization of citrate as a sole source of carbon (Simmon's medium at 28° C for 1-3 days): No growth.
 8. Urease (at 28° C for 1-3 days): Positive.
 9. Catalase (Glucose-Yeast extract agar slant at 28° C for one day): Positive.
 10. Temperature for growth (Emerson's medium for one day): Grow at 10° to 45° C. Optimum 25–35° C.
 11. pH for growth (Glucose-Bouillon broth at 28° C for one day): Optimum pH for growth: 6.0–8.0. Not grow at pH 2.55 but grow slightly at pH 4.38.
 12. Oxygen requirement (Mannit-Yeast extract soft agar at 28° C for 3 days): Aerobic.
 13. Production of acids and gases from sugars:
  i. Acid but no gas from: L-arabinose, D-xylose, L-raffinose, D-glucose, D-mannose, D-galactose, D-fructose, maltose, lactose, glycerol, mannitol, sorbitol, and salicine. Acid production from sorbitol is weak.
  ii. Neither acid nor gas from: sucrose, starch and inulin.
 14. Production of acid from ethanol (Yeast extract-peptone at 27° C): Very weak acid production is observed in 1.92% ethanol containing medium but no acid forms at 3.5 and 7.5 %.

The scrutinization of the above physiological properties is made, unless otherwise specified, on the basis of the description in "Manual of Microbiological Methods" 1957, McGraw Hill Book Co. Inc. edited by the Society of American Bacteriologists.

Strain B, 1. ASM-1005 strain, ATCC 21914
A. Observations:
1. Shape of cells (bouillon agar slants and bouillon broth at 30° C for 3 days): Rods, 0.4–0.7 × 0.8–1.4 $\mu$, occurring singly and in pairs with rounded ends. Snapping division is found but no branching is observed.
2. Motility: Motile with monotrichous flagellum.
3. Spore: Not formed.
4. Gram staining (bouillon agar slants, at 30° C for 7 days): Positive.
5. Acid-fast: Negative.

B. Growth on various media:
1. Bouillon agar colonies (30° C, 24–48 hrs.): Circular, smooth, entire, convex, glistening, translucent, orange-yellow.
2. Bouillon agar slant (30° C, 24–72 hrs.): Growth moderate, filiform and butyrous; orange-yellow to orange,
3. Bouillon broth (30° C, 7 days): Moderately turbid; membranous surface growth; viscid sediment; no odor.
4. Bouillon gelatin stab: Liquefaction; at 20° C, liquefaction is observed slightly 2 days later and then becomes saccateform 7 days later, approximately 4 mm in diameter and 7 mm in depth; at 25° and 30° C, a more distinct liquefaction is observed.
5. Litmus milk (30° C, 14 days): Acid; slightly coagulated.
6. Potato slant (30° C, 14 days): Growth poor; pale orange-yellow glistening.
7. Bouillon D-gluconate agar slant (30° C, 72 hrs.) Growth abundant; filiform; viscid bright orange-yellow glistening.

C. Physiological properties (unless otherwise indicated, based on the results of the observation at 30° C within 14 days):
1. Nitrite: Not produced from nitrate.
2. Denitrification: Neither growth nor gas production is observed in paraffin-sealed bouillon broth containing 1 % $KNO_3$.
3. Methyl-red test: Positive.
4. Voges-Proskauer reaction: Negative.
5. Indole: Not produced.
6. Hydrogen sulfide: Produced.
7. Ammonia: Produced slightly.
8. Starch: Not hydrolyzed.
9. Growth on citrate media:
i. Koser's medium: Scant growth.
ii. Christensen's medium: Growth.
10. Growth with inorganic nitrogen sources:
i. Ammonium (Glucose-Hucker's medium): No growth.
ii. Nitrate (Glucose-Dimmick's medium): The medium slightly colored yellowish.
11. Pigment formation: Not formed.
12. Urease: Positive.
13. Catalase: Positive.
14. Oxidase (bouillon agar slant, 18–24 hrs., tetramethylphenylenediamine): Slightly positive.
15. Temperature relations:
i. Temperature of growth: 10°–40° C; No growth at 4° C and 45° C.
ii. Optimum temperature of growth: 28°–35° C.
16. pH relations:
i. pH of growth: 5.0–10.0.
ii. Optimum pH of growth: 6.0–8.0.
17. Oxygen requirement: Facultative; i) Paraffin-sealed stab culture turns yellow uniformly. (7 days at 30° C, Glucose-BCP medium) ii) Growth is observed by Shotensack method after incubation for 16 days.
18. O-F test (Hugh-Leifson's method): Acid is anaerobically produced from D-glucose, but neither acid nor gas is produced from lactose.
19. Production of acids and gases from sugars (Barsiekow's medium):
i. Acid but no gas from D-xylose, D-glucose, D-mannose, D-fructose, D-galactose, maltose, sucrose, trehalose, D-mannitol and glycerol (weak).
ii. Neither acid nor gas from L-arabinose, lactose, D-sorbitol, inositol and starch.
20. Cellulose (Peptone-water + microcrystalline cellulose): Not hydrolyzed.
21. Methylene-blue (bouillon broth, 18–24 hrs.): Reduced.
22. D-gluconic acid: Utilized.
23. 2-Keto-D-gluconic acid: Slightly utilized.

D. Origin: Soil

The above taxonomical properties are compared with the description of Bergey's Manual of Determinative Bacteriology (7th Edition, hereinafter, to be simply referred to as "Manual") to lead to the conclusion that this strain belongs to the genus of Brevibacterium in view of the following observations; being faculative and gram-positive short rods which form no spore, and showing snapping division but no branching.

This strain shows a kind of coincidence with the classification key of Brevibacterium acetylicum in the above manual and is considered to be in a close relation thereto by the features found in the following further observations; being motile, liquifying gelatin, assuming orange-yellow to orange on a bouillon agar slant and its poor growth with pale orange-yellow color on potato agar slant.

However this strain still has other taxonomical properties which are widely different from those of Brevibacterium acetylicum described in the above manual in that: different characteristics of the colonies and of the bouillon broth cultures; acidified litmus milk and weak coagulation thereof; no peptonization; no hydrolyzation of starch; a relatively high optimum temperature of growth at 28°–35° C and a negative Voges-Proskauer's reaction.

Furthermore, since this strain does not show a coincidence with any other known species of the genus, it (ASM-1005 strain) is considered to belong to a new species, and has been named as Brevibacterium ketosoreductum nov. sp. by the present inventors.

Strain B, 2. ASM-856-4 strain, ATCC No. 31083.

This strain forms two kinds of colonies, i.e., a smooth colony and a rough colony, on bouillon agar; the majority of the colonies being smooth ones and interconversion between the smooth and the rough colonies being observed.

Unless otherwise indicated, the data listed below are described as the common characteristics of both colonies.

A. Observations:
1. Shape of cells (bouillon agar slants and bouillon broth at 30° C for 2 days): Short rods of 0.6–0.8 ×

1.2–1.6 μ with rounded ends, occurring singly or in pairs. Snapping division is found but no branching is observed.

2. Motility: Non motile.
3. Spore: Not formed.
4. Gram staining (bouillon agar slant, at 30° C for 7 days): Positive.
5. Acid-fast: Negative.

B. Growth on various media:
1. Bouillon agar colonies (30° C, 24–48 hrs.):
  a. Smooth colony: Circular, smooth, entire, effuse or raised, glistening, translucent and pale yellow.
  b. Rough colony: Circular, rough, curled, effuse, dull, translucent and pale yellow.
2. Bouillon agar slant (30° C, 24–72 hrs): Growth moderate, filiform and butyrous; pale yellow.
3. Bouillon broth (30° C, 7 days):
  a. Smooth colony: Slight turbid; no surface growth; flaky sediment and no odor.
  b. Rough colony: Clear, no surface growth; flocculent sediment and no odor.
4. Bouillon gelatin stab (20° C and 30° C, 21 days): No liquefaction.
5. Litmus milk (30° C, 21 days):
  a. Smooth colony: Weak acid. b. Rough colony: Weak acid in upper layer; coagulation and reduction in lower layer; no peptonization.
6. Potato slant (30° C, 14 days): Growth moderate, filiform, glistening, and slightly reddish yellow.

C. Physiological properties (unless otherwise indicated, based on the results of the observations at 30° C within 14 days):
1. Nitrite: Not produced from nitrate.
2. Denitrification (Paraffin-sealed bouillon broth containing 1 % $KNO_3$): Not observed.
3. Methyl-red test: Negative.
4. Voges-Proskauer reaction: Negative.
5. Indole: Not produced.
6. Hydrogen sulfide: Produced.
7. Ammonia: Not produced.
8. Starch: Hydrolyzed.
9. Growth on citrate media:
i. Koser's Medium: No growth.
ii. Simmons' medium: No growth.
iii. Christensen's medium: Growth.
10. Growth with inorganic nitrogen sources:
i. Ammonium (Glucose-Hucker's medium*): Growth.
ii. Nitrate (Glucose-Dimmick's medium*): Growth.
* A vitamin mixture is added.
11. Pigment: Not produced.
12. Urease: Negative.
13. Catalase: Positive.
14. Oxidase (bouillon agar slant, 18–24 hrs., tetramethylphenylenediamine): Positive.
15. Temperature relations:
i. Temperature of growth (72 hrs.): 10°–40° C; No growth at 5° and 45° C.
ii. Optimum temperature of growth (24 hrs.): 20°–35° C.
16. pH relations:
i. pH of growth (72 hrs.): 5.0–10.0.
ii. Optimum pH of growth (24 hrs.): 6.0–7.0.
17. Oxygen requirement: Aerobic.
18. O-F test (Hugh-Leifson's method): Acid is anaerobically produced from D-glucose. The top layer of paraffin-sealed stab culture is slightly yellowed. No acid and gas is produced from lactose.

19. Production of acids and gases from sugars (Barsiekow's medium):
  a. Smooth colony:
    i. Acid but no gas from L-arabinose, D-xylose, D-glucose, D-mannose, D-fructose, D-galactose, maltose, sucrose and D-mannitol.
    ii. Neither acid nor gas from lactose, trehalose, D-sorbitol, inositol, glycerol and starch.
  b. Rough colony:
    i. Acid but no gas from D-glucose, D-mannose, D-fructose, D-galactose, maltose, sucrose, lactose (weak) and D-mannitol.
    ii. Neither acid nor gas from L-arabinose, D-xylose, trehalose, D-sorbitol, inositol, glycerol and starch.
20. Cellulose (Peptone-water + microcrystalline cellulose): Not hydrolyzed.
21. Methylene blue (bouillon broth, 18–24 hrs.): Not reduced.
22. D-gluconic acid: Utilized.
23. 2-Keto-D-gluconic acid: Utilized.

D. Origin: Soil.

The above taxonomical properties are compared with the description in the "Manual" to lead to the conclusion that this strain belongs to the genus of Brevibacterium in view of the following observations; being gram-positive short rods which form no spore, and showing snapping division but no branching. However, in the genus of Brevibacterium described in the "Manual", no pertinent species is found. Therefore this strain is considered to be a new strain.

Strain B, 3. ASM-3356-31 strain, ATCC No. 31082.

A. Observations:
1. Shape of cells (bouillon agar slant and bouillon broth at 30° C for 2 days): Short rods of 0.7–0.9 × 0.9–1.6 μ with rounded ends, occurring singly or in pairs. Snapping division is found but no branching is observed.
2. Motility: Motile with single flagellum.
3. Spore: Not formed.
4. Gram staining (bouillon agar slant at 30° C for 7 days): Positive.
5. Acid-fast: Negative.

B. Growth on various media:
1. Bouillon agar colonies (30° C, 24–48 hrs.): Circular, smooth, entire, effuse, glistening, translucent and vivid orange.
2. Bouillon agar slant: Growth abundant, filiform, butyrous and vivid orange.
3. Bouillon broth (30° C, 7 days): Moderately turbid, membranous surface growth, flocculent sediment, and no odor.
4. Bouillon gelatin stab (20° C and 30° C): Liquefaction; at 20° C, liquefaction is observed slightly in 3 days later but its progress is very slow, and becomes stratiform on and after 12th day, approximately 8 mm in depth; at 30° C, liquefaction is more remarkable and proceeds more rapidly.
5. Litmus milk (30° C, 25 days): Weakly acidified and coagulated; intensely peptonized.
6. Potato slant (30° C, 7 days): Growth moderate, filiform, glistening and light orange.

C. Physiological properties (unless otherwise indicated, based on the results of the observation at 30° C within 14 days):
1. Nitrite: Not produced from nitrate.

2. Denitrification (Paraffin-sealed bouillon broth containing 1% $KNO_3$): Not observed.
3. Methyl-red test: Positive.
4. Voges-Proskauer reaction: Negative.
5. Indole: Not produced.
6. Hydrogen sulfide: Produced.
7. Ammonia: Not produced.
8. Starch: Not hydrolyzed.
9. Growth on citrate media:
  i. Koser's medium: No growth.
  ii. Simmons' medium: No growth.
  iii. Christensen's medium: Growth.
10. Growth with inorganic nitrogen sources:
  i. Ammonium (Glucose-Hucker's medium*): Growth.
  ii. Nitrate (Glucose-Dimmick's medium*): Growth.
* A vitamin mixture is added.
11. Pigment: Not produced.
12. Urease: Negative.
13. Catalase: Positive.
14. Oxidase (Bouillon agar slant, 18-24 hrs., tetramethylphenylenediamine): Positive.
15. Temperature relations:
  i. Temperature of growth (72 hrs.): 10°-38° C; No growth at 5° and 43° C.
  ii. Optimum temperature of growth (24 hrs.): 20°-37° C.
16. pH relations:
  i. pH of growth (72 hrs.): 5.0-11.0.
  ii. Optimum pH of growth (24 hrs.): 6.0-8.0.
17. Oxygen requirement: Aerobic (Paraffin-sealed stab culture is yellowed in the whole layer; No growth at an anaerobic condition, prepared by the modified von Kovacs-Zorkoczy's method.)
18. O-F test (Hugh-Leifson's method): Acid is anerobically produced from both D-glucose and lactose (The whole layer of paraffin-sealed stab culture is yellowed).
19. Production of acids and gases from sugars (Barsiekow's medium):
  i. Acid but no gas from L-arabinose, D-xylose, D-glucose, D-mannose, D-fructose, D-galactose, maltose, sucrose, lactose, trehalose and D-mannitol.
  ii. Neither acid nor gas from D-sorbitol, D-inositol, D-glycerol and starch.
20. Cellulose (Peptone-water + microcrystalline cellulose): Not hydrolyzed.
21. Methylene blue (bouillon broth, 18-24 hrs.): Reduced.
22. D-gluconic acid: Utilized.
23. 2-Keto-D-gluconic acid: Utilized.
D. Origin: Soil.

The above taxonomical properties are compared with the description of the "Manual" to lead to the conclusion that this strain belongs to the genus of Brevibacterium in view of the following observations; being gram-positive short rods which form no spore and showing snapping division.

As a result of the comparison of the properties of this strain with those of the previously-described No. ASM-1005 strains, this No. ASM-3356-31 strain is regarded as a variant of the *Brevibacterium ketosoreductum* strain in view of the substantial coincidence in the properties of both of these strains with some exceptions in the difference in the behaviors for litmus milk and oxygen, urea, and in the reaction against sugars (L-arabinose, lactose and glycerine).

Strain B, 5. ASM-3311-6 strain, ATCC No. 31081.
A. Observations:
1. Shape of cels(bouillon agar slant and bouillon broth at 30° C for 2 days): Rods of 0.8-1.0 × 1.2-2.1 $\mu$ with rounded ends, occurring singly or in pairs. Snapping division is found. Pleomorphism; branching and club type are observed in the respective phases of growth.
2. Motility: Motile with single flagellum.
3. Spore: Not formed.
4. Gram-staining (bouillon agar slant, at 30° C for 7 days): Positive.
5. Acid-fast: Negative.
B. Growth on various media:
1. Bouillon agar colonies (30° C, 24-48 hrs.): Circular, smooth, entire, unbonate, glistening translucent and vivid reddish yellow.
2. Bouillon agar slant (30° C, 24-72 hrs.): Growth abundant, filiform, butyrous and bright reddish yellow.
3. Bouillon broth (30° C, 7 days): Slight turbid, flocculent sediment; on and after 7th day of the culture, ringed surface growth along the test tube wall is found. No odor.
4. Bouillon gelatin stab (20° C and 30° C): Liquefaction; at 20° C, liquefaction is observed on and after 6th day but its progress is very slow and becomes stratiform on and after 16th day, approximately 5 mm in depth; at 30° C, liquefaction is more remarkable and proceeds more rapidly.
5. Litmus milk (30° C, 25 days): Unchanged.
6. Potato slant (30° C, 14 days): Growth abundant, filiform, glistening and vivid yellowish orange.
C. Physiological properties (unless othewise indicated, based on the results of the observations at 30° C within 14 days):
1. Nitrite: Not produced from nitrate.
2. Denitrification (Paraffin-sealed bouillon broth containing 1% $KNO_3$): Not observed.
3. Methyl-red test: Negative.
4. Voges-proskauer reaction: Negative.
5. Indole: Not produced.
6. Hydrogen sulfide: Produced.
7. Ammonia: Not produced.
8. Starch: Hydrolyzed.
9. Growth on citrate media:
  i. Koser's medium: No growth.
  ii. Simmons' medium: No growth.
  iii. Christensen's medium: Growth.
10. Growth with inorganic nitrogen sources:
  i. Ammonia (Glucose-Hucker's medium*): Growth.
  ii. Nitrate (Glucose-Dimmick's medium*): Growth.
* A vitamin mixture is added.
11. Pigment: Not produced.
12. Urease: Negative.
13. Catalase: Positive.
14. Oxidase (Bouillon agar slant, 18-24 hrs., Tetramethylphenylenediamine): Positive.
15. Temperature relations:
  i. Temperature of growth (72 hrs.): 10°-40° C. No growth at 5° C and 45° C.
  ii. Optimum temperature of growth (24 hrs.): 15°-35° C.
16. pH relations:
  i. pH of growth (72 hrs.): 5.0-11.0.
  ii. Optimum pH of growth (24 hrs.): 8.0-9.0.
17. Oxygen requirement: Aerobic.

18. O-F test (Hugh-Leifson's method): Acid is only aerobically produced from D-glucose. Negative against lactose.

19. Production of acids and gases from sugars (Barsiekow's medium):
   i. Acid but no gas from L-arabinose, D-xylose, D-glucose, D-mannose, D-fructose, D-galactose, maltose, sucrose, trehalose, D-mannitol and glycerine.
   ii. Neither acid nor gas from lactose, inositol, D-sorbitol and starch.

20. Cellulose (Peptone-water + microcrystalline cellulose): Not hydrolyzed.

21. Methylene-blue (bouillon broth, 18–24 hrs.): Not reduced.

22. D-gluconic acid: Utilized.

23. 2-Keto-D-gluconic acid: Utilized.

24. Lactic acid (Glucose bouillon broth, 48 and 96 hrs.): Not produced from D-glucose.

25. Heat tolerance (10% skimmed milk solution, 72° C, 10 min.): Negative.

D. Origin: Soil.

The above taxonomical properties are compared with the description of the "Manual" to lead to the conclusion that this strain belongs to the genus of Corynebacterium in viewb of the following observations; being gram-positive short rods which form no spore, showing snapping division, having pleomorphism of branching and club type, being unable to hydrolyze cellulose and to produce lactic acid, and having no heat tolerance.

This strain is therefore named by the present inventors as *Corynebacterium sp.* No. ASM-3311-6. Strain B, 6. ASM-20A-77 Strain ATCC No. 31090.

A. Observations:
   1. Shape of cells (bouillon agar slants and bouillon broth at 30° C for 2 days): Rods, 0.6–0.8 by 0.9–2.1 $\mu$, occurring singly and in pairs with rounded ends. Snapping division, branching and club types are observed.
   2. Motility: Non-motile.
   3. Spore: Not formed.
   4. Gram staining (bouillon agar slants, at 30° C for 7 days): Gram-variable.
   5. Acid-fast: Negative.

B. Growth on various media:
   1. Bouillon agar colonies (30° C, 24–48 hrs.): Circular, smooth, entire, convex, glistening, translucent, and bright yellow.
   2. Bouillon agar slant (30° C, 24–72 hrs.): Growth abundant, filiform and butyrous, and bright greenish yellow.
   3. Bouillon broth (30° C, 7 days): Slight turbid; Surface pellicle growth is observed within 4 days; Flaky sediment; No odor.
   4. Bouillon gelatin stab: Liquefaction: at 20° C, liquefication is observed slightly at 14th day and then changes from infundibuliform to stratiform on extended culture; at 30° C, distinct liquefaction is observed.
   5. Litmus milk (30° C, 21 days): Peptonization begins on 11th day and is completed after 3 weeks. The pH becomes slightly alkaline at the early stage of culture and then acidic at the late stage. Litmus is reduced in the lower layer. Surface pellicle growth and light yellow sediment are observed. No coagulation is observed.
   6. Potato slant (30° C, 14 days): Growth abundant; bright greenish yellow glistening.

C. Physiological properties (unless otherwise indicated, based on the results of the observation at 30° C within 14 days):
   1. Nitrite: Nitrite is not produced from nitrate.
   2. Denitrification: Neither growth nor gas production is observed in paraffin-sealed bouillon broth containing 1% $KNO_3$.
   3. Methyl-red test: Negative.
   4. Voges-Proskauer reaction: Negative.
   5. Indole: Not produced.
   6. Hydrogen sulfide: Not produced.
   7. Ammonia: Not produced.
   8. Starch: Hydrolyzed.
   9. Growth on citrate media:
      i. Koser's medium*: No growth.
      ii. Simmon's medium*: Growth.
      iii. Christensen's medium: Growth.
   * Vitamin mixture added.
   10. Growth with inorganic nitrogen sources:
      i. Ammonium (Glucose-Hucker's medium**): Growth.
      ii. Nitrite (Glucose-Dimmick's medium**): Growth.
   ** Vitamin mixture added.
   11. Pigment: Not produced.
   12. Urease: Negative.
   13. Catalase: Positive.
   14. Oxidase (bouillon agar slant, 18–24 hrs., tetramethylphenylenediamine): Positive.
   15. Temperature relations:
      i. Temperature of growth (72 hrs): 10.0°–38.0° C.
      ii. Optimum temperature of growth (24 hrs): 23.0°–28.0° C.
   16. pH relations:
      i. pH of growth (72 hrs.): 6.0–10.0.
      ii. Optimum pH of growth (24 hrs): 7.0–8.0.
   17. Oxygen requirement: Aerobic.
   18. O-F test (Hugh-Leifson's method): Acid is only aerobically produced from D-glucose, but neither acid nor gas is produced from lactose.
   19. Production of acids and gases from sugars (Barsiekow's medium):
      i. Acid but no gas from L-arabinose, D-xylose, D-glucose, D-mannose, D-fructose, D-galactose, maltose, sucrose, and starch.
      ii. Neither acid nor gas from lactose, trehalose, D-sorbitol, D-mannitol, inositol, and glycerol.
   20. Cellulose (Peptone-water + microcrystalline cellulose): Not hydrolyzed.
   21. Methylene-blue (bouillon broth, 18–24 hrs.): Reduced.
   22. D-gluconic acid: Utilized.
   23. 2-Keto-D-gluconic acid: Slightly utilized.

Strain B, 7. ASM-T-13 Strain, ATCC 31089.

A. Observations:
   1. Shape of cells (bouillon agar slants and bouillon broth at 30° C for 2 days): Rods, 0.8–0.9 by 1.0–1.3 $\mu$, occurring singly and in pairs with rounded ends. Snapping division, branching and club types are observed.
   2. Motility: Non-motile.
   3. Spore: Not formed.
   4. Gram staining (bouillon agar slants, at 30° C for 7 days): Positive.
   5. Acid-fast: Negative.

B. Growth on various media:
   1. Bouillon agar colonies (30° C, 24–48 hrs.): Circular, smooth, entire, convex, glistening, translucent, and light yellowish orange.

2. Bouillon agar slants (30° C, 24–72 hrs.): Growth moderate, filiform, butyrous, and light reddish yellow.

3. Bouillon broth (30° C, 7 days): Slight turbid: No surface growth is observed; Flocculent to flaky sediment; No odor.

4. Bouillon gelatin stab: No liquefaction.

5. Litmus milk (30° C, 21 days): Unchanged within 4 days. After 8 days, becoming alkaline, and very weakly coagulated. On and after 16th day litmus completely and uniformly reduced. Very weakly peptonized and not coagulated.

6. Potato slant (30° C, 14 days): Growth moderate; bright yellow glistening.

C. Physiological properties (unless otherwise indicated, based on the results of the observation at 30° C within 14 days):

1. Nitrite: Nitrite is not produced from nitrate.
2. Denitrification: Neither growth nor gas production is observed in paraffin-sealed bouillon broth containing 1% $KNO_3$.
3. Methyl-red test: Negative.
4. Voges-Proskauer reaction: Negative.
5. Indole: Not produced.
6. Hydrogen sulfide: Not produced.
7. Ammonia: Not produced.
8. Starch: Weakly hydrolyzed.
9. Growth on citrate media:
  i. Koser's medium*: No growth.
  ii. Simmon's medium*: No growth.
  iii. Christensen's medium: Growth.
* Vitamin mixture added.
10. Growth with inorganic nitrogen sources:
  i. Ammonium (Glucose-Hucker's medium**): No growth.
  ii. Nitrate (Glucose-Dimmick's medium**): No growth.
** Vitamin mixture added.
11. Pigment: Not produced.
12. Urease: Negative.
13. Catalase: Positive.
14. Oxidase (bouillon agar slant, 18–24 hrs., tetramethylphenylenediamine): Positive.
15. Temperature relations:
  i. Temperature of growth (72 hrs): 10.0°–38.0° C.
  ii. Optimum temperature of growth (24 hrs): 23.0°–28.0° C.
16. pH relations:
  i. pH of growth (72 hrs): 6.0–8.0.
  ii. Optimum pH of growth (24 hrs): 7.0–8.0.
17. Oxygen requirement: Aerobic.
18. O-F test (Hugh-Leifson's method): Acid is slightly produced both aerobically and anaerobically from D-glucose*, but neither acid nor gas is produced from lactose. (*The top layer of paraffin-sealed stab-culture turns yellow as normal stab-culture).
19. Production of acids and gases from sugars (Barsiekow's medium):
  i. Acid but no gas from L-arabinose, D-xylose, D-glucose, D-mannose, D-fructose, D-galactose, maltose, lactose, trehalose, D-sorbitol (weak), D-mannitol, sucrose, and glycerol.
  ii. Neither acid nor gas from inositol, and starch.
20. Cellulose (Peptone-water + microcrystalline cellulose): Not hydrolyzed.
21. Methylene-blue (bouillon broth, 18–24 hrs.): Not reduced.
22. D-gluconic acid: Slightly utilized.
23. 2-Keto-D-gluconic acid: Slightly utilized.

Strain B, 8. ASM-K-106 Strain, ATCC No. 31088.

A. Observations:

1. Shape of cells (bouillon agar slants and bouillon broth at 30° C for 2 days): Rods, 0.6–0.7 by 1.0–1.3 $\mu$, occurring singly and in pairs with rounded ends. Snapping division, branching and club types are observed.

2. Motility: Non-motile.
3. Spore: Not formed.
4. Gram straining (bouillon agar slants, at 30° C for 7 days): Positive.
5. Acid-fast: Negative.

B. Growth on various media:

1. Bouillon agar colonies (30° C, 24–48 hrs.): Circular, smooth, entire, raised, glistening, translucent, and bright yellow.

2. Bouillon agar slant (30° C, 24–48 hrs.): Growth abundant, filiform and butyrous, and bright greenish yellow.

3. Bouillon broth (30° C, 7 days): Slight turbid; Surface pellicle growth is observed within 4 days; Flaky sediment; No odor.

4. Bouillon gelatin stab: Liquefaction: At 20° C, liquefaction is observed Slightly on 14th day and then changes from infundibuliform to stratiform on extended culture; at 30° C, distinct liquefaction is observed.

5. Litmus milk (30° C, 21 days): Peptonization begins on 11th day and is completed after 3 weeks. The pH becomes slightly alkaline at the early stage of culture and then acidic at the late stage. Litmus is reduced in the lower layer. Surface pellicle growth and light yellow sediment are observed. No coagulation is observed.

6. Potato slant (30° C, 14 days): Growth abundant; bright yellow glistening.

C. Physiological properties (unless otherwise indicated, based on the results of the observation at 30° C within 14 days):

1. Nitrite: Nitrite is produced from nitrate.
2. Denitrification: Neither growth nor gas production is observed in paraffin-sealed bouillon broth containing 1% $KNO_3$.
3. Methyl-red test: Negative.
4. Voges-Proskauer reaction: Negative.
5. Indole: Not produced.
6. Hydrogen sulfide: Not produced.
7. Ammonia: Not produced.
8. Starch: Hydrolyzed.
9. Growth on citrate media:
  i. Koser's medium*: No growth.
  ii. Simmon's medium*: Growth.
  iii. Christensen's medium: Growth.
* Vitamin mixture added.
10. Growth with inorganic nitrogen sources:
  i. Ammonium (Glucose-Hucker's medium**):- Growth.
  ii. Nitrate (Glucose-Dimmick's medium**): Growth.
** Vitamin mixture added.
11. Pigment: Not produced.
12. Urease: Negative.
13. Catalase: Positive.
14. Oxidase: (bouillon agar slant, 18–24 hrs., tetramethylphenylenediamine): Positive.
15. Temperature relations:
  i. Temperature of growth (72 hrs): 10.0–38.0° C.
  ii. Optimum temperature of growth (24 hrs): 23.0°–30° C.
16. pH relations:

i. pH of growth (72 hrs): 6.0–9.0.
ii. Optimum pH of growth (24 hrs): 7.0.
17. Oxygen requirement: Aerobic.
18. O-F test (Hugh-Leifson's method): Acid is slightly produced both aerobically and anaerobically from D-glucose*, but neither acid nor gas is produced from lactose. (* The top layer of paraffin-sealed stab-culture turns yellow as normal stab-culture.)
19. Production of acids and gases from sugars (Barsiekow's medium):
   i. Acid but no gas from L-arabinose, D-xylose, D-glucose, D-mannose, D-fructose, D-galactose, maltose, sucrose, lactose (weak), D-mannitol (weak), and starch.
   ii. Neither acid nor gas from trehalose, D-sorbitol, inositol, and glycerol.
20. Cellulose (Peptone-water + microcrystalline cellulose): Not hydrolyzed.
21. Methylene-blue (bouillon broth, 18–24 hrs.): Reduced.
22. D-gluconic acid: Utilized.
23. 2-Keto-D-gluconic acid: Slightly utilized.

The taxonomical properties of the above three strains are compared with the description of the "Manual" to lead to the conclusion that these strains belong to the genus of Corynebacterium in view of the observations which are identical with that of the previously described ASM-3311-6 strain.

Any mutated or modified strains obtained by artificially or inductively mutating the aforedefined microorganism strains, with a treatment by means of, for instance, ultraviolet or X-ray irradiation, or a chemical mutagen such as nitrogen mustard, may likewise be utilized in the method of this invention with advantages.

In the method of this invention, the aforedescribed strains may be inoculated with and incubated in a medium which includes the aforedefined substrate and the cells of such strain, for instance, resting cells or any processed product obtained from the cells may be used to act directly on the substrate. Any means per se known as a method in connection with the incubation technique for microorganisms may be adopted through the use of aerated and agitated submerged fermenters is particularly preferred. A preferred result may be obtainable from an incubation which utilizes a liquid broth medium.

As regards the nutrient medium available for the incubation of the microorganism, although no special restriction is imposed on its class, an aqueous nutrient medium suitably including carbon sources, nitrogen sources, other inorganic salts, small amounts of other nutrients and the like, which can be utilized by the microorganism is desirable for the advantageous incubation of the microorganism. Various nutrient materials which are generally used for the better growth of microorganisms may suitably be included in the medium.

The nitrogen source includes inorganic or organic nitrogen compounds, or compositions containing such compounds which may be exemplified by ammonium salts, nitrate salts, corn steep liquor, peptone, meat extract, bean powder, wheat gluten, yeast extract, yeasts and urea.

The carbon sources which may be included in the medium as the substrate can be exemplified as polyhydric alcohols or sugars such as glucose, glycerol, sucrose, lactose, dextrine, maltose and molasses in addition to the starting material, D-glucose.

Salts of, for instance, calcium, magnesium, potassium, zinc, copper, iron and other metals are employed as the inorganic salts.

For the advantageous performance of the incubation, any suitable factor which can promote the formation of the end product may be added to the medium.

The mixing ratio of these nutrients and the amounts of each ingredient may vary with the generic property of the strains employed, the amounts of the starting material, D-glucose, the amount of one of the strains to be inoculated with respect to the other and the times of inoculations, and the other attendant conditions of the incubation may be selected or determined in accordance with the particulars of the individual case.

Although the concentration of the starting material, D-glucose, in the medium may also be varied with the generic character and the like of the employed strain, a concentration of about 20–200 g/l is generally applicable and, inter alia, a concentration of about 20–100 g/l is preferred.

The conditions of the incubation may also vary with the species and generic character of the strain employed, the composition of the medium and other attendant factors, and may, of course, be selected or determined in accordance with the particulars of the individual cases in order to yield the intended product most efficiently, although an incubation temperature of about 20°–35° C and a pH value of the medium of about 4–9 may preferably be maintained. Normally, an incubation period ranging from 10 hours to 100 hours may be sufficient and the formation of the intended product in the medium reaches its maximum value within such period.

In order to maintain the pH value of the medium to that most suitable for the enzymatic activity of the substance which is produced by the microorganism, any suitable acidic or basic agent may be added to the medium in a suitable amount at a suitable time during the incubation. The same object may alternatively be accomplished by initially incorporating a suitable buffer into the medium at the beginning of the incubation.

The required total amount of the starting material, D-glucose, may be incorporated in the medium all at once at the beginning of the incubation or may be added to the medium in portions at any time during the incubation.

In addition to the previously-described incubation of the microorganism strain, the process of the present invention affords another means wherein the cells of the microorganism, i.e., resting cells, acetone treated cells, lyophilized cells, the ground product thereof and the like which retain an enzymatic activity, are contacted directly with the medium containing the starting material, D-glucose.

Furthermore, the cultured broth of Strain A may be contacted with any processed product of Strain B, or medium containing the intermediate which had previously been produced by the contact with Strain A may be used as a substrate for culturing Strain B for the production of the intended product.

In such cases of direct contact of the cells or the processed product thereof with the substrate, the conditions of the temperatures, pH values and the like being the same as or similar to the case of the incubation of the strain itself, may be employed as far as the cells or the processed product may retain an enzymatic activity for the purpose. Moreover, any buffer solution may suitably be used to maintain the pH value of the reaction mixture constant.

The 2,5-diketo-D-gluconic acid produced by culturing Strain A in the medium or by the direct contact of the substrate with any processed product of Strain A and accumulated in a broth of crude state, may be, without being isolated, utilized by Strain B or reduced by any processed product of Strain B to be converted into 2-keto-L-gulonic acid. Alternately, the 2-keto-D-gluconic acid which would be by-produced, if the pure, unmixed culture of Strain B should be conducted, can be utilized by Strain A or oxidized by any processed product of Strain A to produce 2,5-diketo-D-gluconic acid which may subsequently be converted again into 2-keto-L-gulonic acid.

The 2-keto-L-gulonic acid thus produced and accumulated in the medium may be separated and purified by any per se known conventional means which suitably utilizes the property of the product, and it may be separated as the free acid or as a salt of sodium, potassium, calcium, ammonium or the like.

In the case where the 2-keto-L-gulonic acid is obtained in its free state, it may be converted into any salts of, for instance, sodium, potassium, calcium, ammonium or the like by any suitable per se known means, while if the process yields a salt, the salt may be converted into its free acid or into any other salts by any suitable means.

Any method as may be available for the separation of the intended product from the medium can be employed unless the method used would detract from the object of the present invention. For instance, the separation may be performed in any suitable combination or repetition of the following unit processes; a) removal of the cells of the microorganisms from the fermented broth by filtration, centrifugation or treatment with active charcoal, b) precipitation of the intermediate crystals by concentrating the filtered broth, c) recovery of the precipitated crystals by filtering or centrifuging the concentrated broth, d) recrystallization of the intermediate crystals, e) extraction with solvent, and f) fractionation by chromatography,.

The identification of the 2-keto-L-gulonic acid obtained by the method of this invention may be performed by, for instance, elemental analysis as well as measurement of physiochemical properties such as melting point, spectrum of infrared absorption, optical rotation and the like.

DESCRIPTION OF THE PREFERRED EMBODIMENTS

In the following, the process of the present invention will be illustrated in more detail by way of examples.

EXAMPLE 1.

1. Seed cultures:

In this experiment, *Acetomonas albosesamae* ATCC 21998 represented the Strain A, whereas strains of the species listed in Table 1 were employed as the Strain B. One loopful of the individual strains was inoculated in the media of the following compositions, each 100 ml thereof being placed in a shaker flask of 500 ml, its pH value being adjusted to 7.0 before sterilization (115° C, 20 min.). Shaking cultures were performed on a rotary shaker (240 rpm) at 30° C. for 15 hours.

| Seed media: | for Strain A, | for Strain B. |
|---|---|---|
| D-glucose | 0.2% | |
| Glycerol | | 0.2% |
| Yeast Extract | 0.1% | 0.2% |
| Polypeptone | 0.5% | 0.2% |
| Potassium phsphate, monobasic | 0.1% | 0.1% |
| Magnesium sulfate . 7H₂O | 0.05% | 0.02% |

2. Preliminary preparations:

In the runs wherein the 2,5-diketo-D-gluconic acid contained in a cultured broth is employed for the production of the end product, namely, the mixed culturing of the present invention, such cultured broth had previously been prepared by inoculating said seed culture of the Strain A on a fermentation medium containing:

| D-glucose | 5.0% |
| Yeast Extract | 0.2% |
| Polypeptone | 0.6% |
| Potassium phosphate, monobasic | 0.1% |
| Magnesium sulfate . 7H₂O | 0.02% and |
| Calcium carbonate | 1.75% | each 100 ml thereof being placed in a shaker flask of 500 ml, its pH value being adjusted to 7.0 before sterilization (115° C, 20 min.) with a volumetric inocolumn size of 10%, followed by a shaking culture (24 hours) in a similar manner. Alternately, a medium containing

| D-glucose | 0.2% |
| Yeast Extract | 0.4% |
| Polypeptone | 0.4% |
| Potassium phosphate, monobasic | 0.2% and |
| Magnesium sulfate . 7H₂O | 0.04% | was prepared for the fermentation medium of the Strain B. Each 50 ml of the medium, its pH value being adjusted to 7.0 before sterilization (115° C, 20 min.), is placed in a shaker flask of 500 ml and there is added each 5 ml of the seed culture of the Strain B.

3. Mixed culture:

In addition to the previously described culture broth of the Strain A which was used in the process of the present invention without any previous treatment such as sterilization by filtration, sterilized broth of the same culture as well as an aqueous solution (5%) of pure calcium 2,5-diketo-D-gluconate (sterilized by filtration) were used in control runs performed in parallel.

These 2,5-diketo-D-gluconic acid containing solutions are added to the individual fermentation broths of the Strain B, at the beginning and after the incubation (240 rpm, 30° C) for 24 hours in a manner that the final concentration of the 2,5-diketo-D-gluconic acid in the mixtures is 2.5%. The incubations were continued thereafter under the same conditions for 72 hours, respectively.

The results of the incubations are summarized in Table I which support the advantageous features of the mixed culturing process of the present invention wherein the product being completely free of by-production of the undesirable optical isomer, 2-keto-D-gluconic acid while both of the control runs indicate the attendant by-production of 2-keto-D-gluconic acid with the end product, 2-keto-L-gulconic acid.

4. Quantitative determination:

Gas chromatography (Column, Silicone gum SE-52: Sample, sylilated).

was incorporated into the cultured broth of the Strain B which had previously been incubated for 24 hours.

Table II summarizes the results of the quantitative determination of the cultured brothes by gas chromatography performed as described in Example 1 as well Table 1

| | | Added 2,5-diketo-D-gluconic acid | | | | | |
|---|---|---|---|---|---|---|---|
| Accumulation of 2-keto-L-gulonic acid (2KLG) or 2-keto-D-gluconic acid (2KDG) (mg/ml) | | | | | | | |
| | Time of addition (hrs. after the initiation of the incubation | Cultured broth of *Acetomonas albosesamae* | | | | Aqueous solution of calcium salt | |
| | | Mixed culturing (without sterilizaton) | | Pure, unmixed, culturing with sterilization by filtration | | | |
| Strain B | | 2KLG | 2KDG | 2KLG | 2KDG | 2KLG | 2KDG |
| *Brevibacterium sp.* ASM-856-4 | 0 | 0.58 | 0 | 1.16 | 0.20 | 0.84 | 0.16 |
| FERM-P 2686, ATCC 31083 | 24 | 2.24 | 0 | 2.86 | 0.30 | 2.49 | 0.21 |
| *Brevibacterium sp.* ASM-3356-31 | 0 | 0.42 | 0 | 0.25 | 0.08 | 0.19 | 0.05 |
| FERM-P 2685, ATCC 31082 | 24 | 1.19 | 0 | 1.61 | 0.75 | 1.51 | 0.51 |
| *Brevibacterium testacium* | 0 | 0.11 | 0 | 0.09 | 0.01 | — | — |
| IFO 12675 | 24 | 0.14 | 0 | 0.12 | 0.02 | — | — |
| *Corynebacterium sp.* ASM-3311-6 | 0 | 1.40 | 0 | 0.23 | 0.07 | 0.18 | 0.59 |
| FERM-P 2687, ATCC 31081 | 24 | 1.75 | 0 | 1.18 | 1.04 | 0.95 | 0.74 |
| *Brevibacterium ketosoreductum* | 0 | 0.34 | 0 | 0.64 | 0.34 | 0.49 | 0.22 |
| ASM-1005, FERM-P 1905, ATCC 21914 | 24 | 1.26 | 0 | 1.77 | 0.85 | 1.23 | 0.69 |
| *Corynebacterium sp.* ASM-20A-77 | 0 | 1.33 | 0 | 1.17 | 0.22 | 1.23 | 0.34 |
| FERM-P 2770, ATCC 31090 | 24 | 4.48 | 0 | 4.13 | 1.78 | 4.15 | 1.46 |
| *Corynebacterium sp.* ASM-T-13 | 0 | 0.84 | 0 | 0.72 | 0.16 | 0.65 | 0.25 |
| FERM-P 2771, ATCC 31089 | 24 | 1.17 | 0 | 1.08 | 0.32 | 0.96 | 0.19 |
| *Corynebacterium sp.* ASM-K-106 | 0 | 0.76 | 0 | 0.54 | 0.02 | 0.80 | 0.05 |
| FERM-P 2769, ATCC 31088 | 24 | 2.69 | 0 | 2.39 | 0.85 | 2.83 | 0.79 |

EXAMPLE 2

In this experiment, another series of the mixed cultures for the production of 2-keto-L-gulonic acid employing the Strains A and B listed in Table II were performed in a similar manner as described in Example 1, wherein the non-sterilized cultured broth of Strain A as by paper partition chromatography. In each run, no by-production of 2-keto-D-gluconic acid was observed.

Table II

| | Accumulation of 2-keto-L-gulonic acid (mg/ml) | | |
|---|---|---|---|
| | Strain A | | |
| Strain B | *Acetomonas albosesamae* FERM-P 2439 ATCC 21998 | *Acetobacter melanogenum* IFO 3239 | *Gluconobacter rubiginosus* IFO 3244 |
| *Brevibacterium sp.* ASM-856-4 FERM-P 2686 ATCC 31083 | 2.24 | 1.10 | 1.54 |
| *Brevibacterium sp.* ASM-3356-31 FERM-P 2685 ATCC 31082 | 1.19 | 0.75 | 0.98 |
| *Brevibacterium testacium* IFO-12675 | 0.15 | 0.06 | 0.08 |
| *Corynebacterium sp.* ASM-3311-6 FERM-P 2687 ATCC 31081 | 1.75 1.75 | 0.82 0.82 | 1.25 1.25 |
| *Brevibacterium ketosoreductum* ASM-1005 FERM-P 1905 ATCC 21914 | 1.28 | 0.57 | 0.97 |
| *Corynebacterium sp.* ASM-20A-77 FERM-P 2770 ATCC 31090 | 4.48 | 2.02 | 3.49 |
| *Corynebacterium sp.* ASM-T-13 FERM-P 2771 ATCC 31089 | 0.17 | 0.62 | 0.71 |
| *Corynebacterium sp.* ASM-K-106 FERM-P 2769 ATCC 31088 | 2.69 | 0.16 | 1.81 |

COMPARATIVE PREPARATION

Another series of incubations for the production of 2-keto-L-gulonic acid employing the Strain A of Example 1 and some of the Strain B listed in Table III, were performed in a similar manner as described in Example 1 wherein the cultured broths of the Strain A sterilized by filtration were incorporated into the cultured media of the Strain B which had previously been incubated for 24 hours.

Cells in the each broth which had been incubated for another 16 hours, are collected, washed twice with sterilized physiological saline and suspended in Tris Buffer (0.05 mol, pH 7.5, 100 ml) in an incorporation rato of the cells of 4.1 mg (dry weight)/ml.

To this suspension, there was added calcium 2,5-diketo-D-gluconate to give a concentration of 1% and incubation was conducted at 30° C for 24 hours.

At given times during the contacting treatment samples were withdrawn from the mixture to perform a quantitative determination as described in Example 1, which proved the formation of 2-keto-L-gulconic acid at the beginning of the contacting operation. Table III summrizes the results summarizes the treatment. In each run the formation of 2-keto-D-gluconic acid associated with that of 2-keto-L-gulonic acid was observed.

Table III

| Strain B | Accumulaton of 2-keto-L-gulonic acid at the end of the incubation (mg/ml) |
|---|---|
| ASM-856-4 | 1.12 |
| ASM-3356-31 | 0.58 |
| ASM-3311-6 | 0.64 |
| ASM-20A-77 | 1.85 |
| ASM-K-106 | 1.32 |
| ASM-T-13 | 0.55 |

EXAMPLE 3

In this experiment, strains of the species listed in Table IV were employed as the Strain A whereas *Brevibacterium ketosoreductum* ASM-1005, FERM-P 1905, ATCC 21914 solely represented the Strain B.

Seed media for these strains were identical to those described in the beginning of the Example 1 which were treated for the inoculation similarly.

Each one loopful of the individual strains from bouillon slants was inoculated in each 100 of said seed media placed in a shaker flask of 500 ml and shaken on a rotary shaker (220 rpm) at 30° C for 6 hours.

The obtained individual seed cultures of the Strains A and B were mixed together at various ratios of cell concentrations listed in Table IV and inoculated in 5% inoculum as a whole with a fermentation medium containing:

| D-glucose | 2.0% |
|---|---|
| Yeast Extract | 0.5% |
| Polypeptone | 0.5% |
| Potassium phosphate, monobasic | 0.1% |
| Magnesium sulfate . 7H$_2$O | 0.02% and |
| Calcium carbonate | 0.7% | each 100 ml thereof being placed in a shaker flask of 500 ml and, adjusted to pH 7.0 before sterilization, and the shaking cultures of the above condition were continued for 60 hours.

After the incubation, the formation of 2-keto-L-gulonic acid was detected as a pink spot on paper partition chromatography [developing solvent: phenol: water: formic acid (75:25:4), detective agent; anilin-hydrogen-phthalic acid].

In each run no accumulation of the undesirable 2-keto-D-gluconic acid was confirmed by the paper partition chromatography.

The quantitative determination was performed by the gas chromatography as mentioned in Example 1 and the results are summarized in Table IV which indicates no accumulation of 2-keto-D-gluconic acid along with that of 2-keto-L-gulonic acid in each run.

Table IV

| Strain A (In each run, *Brevibacterium ketosoreductum* represents the Strain B.) | Ratio of cell concentration (A:B) | Accumulation of 2-keto-L-gulonic acid (mg/ml) |
|---|---|---|
|  | 1:1 | 0.3 |
| *Acetomonas albosesamae* FERM-P 2439, ATCC 21998 | 1:3 | 0.57 |
|  | 6:1 | 0.1 |
| *Acetobacter melanogenum* IFO 3293 | 1:1 | 0.3 |
| *Gluconobacter rubiginosus* IFO 3244 | 1:1 | 0.23 |

EXAMPLE 4.

The strains identical to Example 3 (Table IV) were employed and the seed cultivation of the Strain B was carried out as described in Example 3.

| A fermentation medium containing: | |
|---|---|
| D-glucose | 10% |
| Yeast Extract | 0.1% |
| Polypeptone | 0.4% |
| Potassium phosphate, monobasic | 0.1% |
| Magnesium sulfate . 7H$_2$O | 0.05% and |
| Calcium carbonate | 3.4% | its pH value adjusted to 7.0 before sterilization, is used for cultivating *Acetomonas albosesamae* of the Strain A.

In another run wherein *Acetobacter melanogenum* or *Gluconobacter rubiginosus* is employed in lieu of *Acetomonas albosesamae*, the percentages of the D-glucose and the calcium carbonate in the above medium are changed to 4.0% and 1.4%, respectively.

Each one loopful of the individual seed cultures of the Strain A is inoculated with these media, respectively, each 50 ml thereof is placed in a shaking flask of 500 ml and sterilized at 120° C for 20 minutes, and incubated as described in Example 3 to produce 2,5-diketo-D-gluconic acid.

At each given time during the incubation listed in Table V, the seed culture broths of the Strain B were incorporated into the broths containing cells of the Strain A (20 ml, when *Acetomonas albosesamae* is employed and 50 ml each, if *Acetobacter melanogenum* or *Gluconobacter rubiginosus* is employed) at various ratios of cell concentrations listed in Table IV and the mixed broth in each 500 ml flask was supplemented to 100 ml with a nutrient liquid followed by shaking for 60 hours after adjustment of the pH value to 6.3 with a sterilized aqueous solution of sodium hydroxide.

The nutrient liquid used as a concentrated mixture of yeast extract and polypeptone (1:1), sterilized at 20° C for 20 minutes, adjusted to pH 7.0, diluted such that the concentration of polypeptone or yeast extract in each of the mixed and supplemented broths becomes 0.2%.

The results of the incubation analyzed in a similar manner as described in Example 3 are summarized in Table V, wherein accumulations of 2-keto-L-gulonic acid are observed in the respective runs while no formation of 2-keto-D-gulconic acid is observed.

Table V

| Strain A (In each run, Brevibacterium ketoso-reductum represents the Strain B.) | Ratio of cell concentration (A:B) | Incubation time (hours) fermentation for 2,5-diketo-D-gluconic acid | mixed culturing | Accumulation of 2-keto-L-gulonic acid (mg/ml) |
|---|---|---|---|---|
| Acetomonas albosesamae | 1:1 | 60 | 60 | 0.95 |
| | 1:10 | 60 | 60 | 1.5 |
| | 3:1 | 60 | 60 | 2.3 |
| Acetobacter melanogenum | 7:1 | 30 | 60 | 0.46 |
| Gluconobacter rubiginosus | 10:1 | 30 | 60 | 0.73 |

EXAMPLE 5.

In this experiment, Acetomonas albosesamae solely represents the Strain A while Brevibacterium ketosoreductum is employed as the Strain B. Both of the medium as well as the method of incubation applied to the Strain A for producing 2,5-diketo-D-gluconic acid were identical to the description in Example 4 whereas the seed cultivation of the Strain B was identical to that of Example 3.

The nutrient liquid used herein contained each 5% of yeast extract and polypeptone, adjusted to pH 7.0 and sterilized at 120° C for 20 minutes.

The seed culture broth of the Strain B (80 ml) in a 500 ml shaker flask was mixed with the fermentation broth containing cells of the Strain A and the accumulated 2,5-diketo-D-gluconic acid (8 ml) to be brought to the shaking operation.

At each time during the incubation, 25 hours and 42 hours after the initiation thereof, 10 ml of the fermentation broth containing the accumulated 2,5-diketo-D-gluconic acid and 5 ml of the nutrient liquid were fed to the mixture which was incubated thereafter for another hours to make the total incubation extend to 90 hours.

As a result of analysis performed as described in Example 3, accumulation of 2-keto-L-gluconic acid which amounts to 1.6 mg/ml was observed whereas no formation of 2-keto-D-gluconic acid was observed.

What is claimed is:

1. A method for producing 2-keto-L-gulconic acid or a salt thereof which comprises cultivating a mixed culture of (1) a microorganism strain capable of producing 2,5-diketo-D-gluconic acid from D-glucose which belongs to the genus Acetobacter, Acetomonas or Gluconobacter or an aqueous medium containing viable cells of said microorganism having the enzymatic activity to produce 2,5-diketo-D-gluconic acid from D-glucose, and (2) a microorganism strain capable of converting 2,5-diketo-D-gluconic acid into 2-keto-L-gulonic acid which belongs to the genus Brevibacterium or Corynebacterium or an aqueous medium containing viable cells of said microorganisms having the enzymatic activity to convert 2,5-diketo-D-gluconic acid into 2-keto-L-gluconic acid, in a medium containing D-glucose whereby a mixed culturing is conducted wherein both of said microorganisms or viable cells thereof are present together in the medium during at least part of the entire cultivation in a condition sufficient to produce and accumulate 2-keto-L-gulonic acid or a salt thereof in the resulting culture liquor, and recovering the 2-keto-L-gulonic acid therefrom.

2. A method as claimed in claim 1, wherein (1) the microorganisms capable of producing 2,5-diketo-D-gluconic acid from D-glucose and (2) the microorganisms capable of converting the 2,5-diketo-D-gluconic acid into 2-keto-L-gulconic acid are incubated in the medium containing D-glucose such that both microorganisms coexist and grow together therein during at least the latter part of the cultivation, whereby 2-Keto-D-gluconic acid produced by the latter microorganism (2) is utilized by the former microorganisms (1) to produce 2,5-diketo-D-gluconic acid which is subsequently converted into 2-keto-L-gulonic acid by the latter microorganism (2).

3. A method as claimed in claim 2, wherein the former microorganism strain belongs to the genus of Acetobacter and the latter microorganisms strain belongs to the genus of Brevibacterium.

4. A method as claimed in claim 2, wherein the former microorganism strain belongs to the genus of Acetomonas and the latter microorganism strain belongs to the genus of Brevibacterium.

5. A method as claimed in claim 2, wherein the former microorganism strain belongs to the genus of Gluconobacter and the latter microorganism strain belongs to the genus of Brevibacterium.

6. A method as claimed in claim 2, wherein the former microorganism strain belongs to the genus of Acetobacter and the latter microorganism strain belongs to the genus of Corynebacterium.

7. A method as claimed in claim 2, wherein the former microorganism strain belongs to the genus of Acetomonas and the latter microorganism strain belongs to the genus of Corynebacterium.

8. A method as claimed in claim 2, wherein the former microorganism strain belongs to the genus of Gluconobacter and the latter microorganism strain belongs to the genus of Corynebacterium.

9. A method as claimed in claim 3, wherein the former microorganism strain belongs to the species which includes Acetobacter melanogenum IFO 3293.

10. A method as claimed in claim 6, wherein the former microorganism strain belongs to the species which includes Acetobacter melanogenum IFO 3293.

11. A method as claimed in claim 4, wherein the former microorganism strain belongs to the species which includes Acetomonas albosesamae ATCC 21998.

12. A method as claimed in claim 7, wherein the former microorganism strain belongs to the species which includes Acetomonas albosesamae ATCC 21998.

13. A method as claimed in claim 5, wherein the former microorganism strain belongs to the species which includes Gluconobacter rubiginosus IFO 3244.

14. A method as claimed in claim 8, wherein the former microorganism strain belongs to the species which includes Gluconobacter rubiginosus IFO 3244.

15. A method as claimed in claim 3, wherein the latter microorganism strain belongs to the species which includes Brevibacterium ketosoreductum ASM-1005, ATCC 21914.

16. A method as claimed in claim 4, wherein the latter microorganism strain belongs to the species which includes Brevibacterium ketosoreductum ASM-1005, ATCC 21914.

17. A method as claimed in claim 5, wherein the latter microorganism strain belongs to the species which includes *Brevibacterium ketosoreductum* ASM-1005, ATCC 21914.

18. A method as claimed in claim 3, wherein the latter microorganism strain belongs to the species which includes *Brevibacterium sp.* ASM-856-4, ATCC 31083.

19. A method as claimed in claim 4, wherein the latter microorganism strain belongs to the species which includes *Brevibacterium sp. ASM*-856-4, ATCC 31083.

20. A method as claimed in claim 5, wherein the latter microorganism strain belongs to the species which includes *Brevibacterium sp.* ASM-856-4, ATCC 31083.

21. A method as claimed in claim 3, wherein the latter microorganism strain belongs to the species which includes *Brevibacterium sp.* ASM-3356-31, ATCC 31082.

22. A method as claimed in claim 4, wherein the latter microorganism strain belongs to the species which includes *Brevibacterium sp.* ASM-3356-31, ATCC 31082.

23. A method as claimed in claim 5, wherein the latter microorganism strain belongs to the species which includes *Brevibacterium sp.* ASM-3356-31, ATCC 31082.

24. A method as claimed in claim 3, wherein the latter microorganism strain belongs to the species which includes *Brevibacterium testaceum* IFO 12675.

25. A method as claimed in claim 4, wheren the latter microorganism strain belongs to the species which includes *Brevibacterium testaceum* IFO 12675.

26. A method as claimed in claim 5, wherein the latter microorganism strain belongs to the species which includes *Brevibacterium testaceum* IFO 12675.

27. A method as claimed in claim 6, wherein the latter microorganism strain belongs to the species which includes *Corynebacterium sp.* ASM-3311-6, ATCC 31081.

28. A method as claimed in claim 7, wherein the latter microorganism strain belongs to the species which includes *Corynebacterium sp.* ASM-3311-6, ATCC 31081.

29. A method as claimed in claim 8, wherein the latter microorganism strain belongs to the species which includes *Corynebacterium sp.* ASM-3311-6, ATCC 31081.

30. A method as claimed in claim 6, wherein the latter microorganism strain belongs to the species which includes *Corynebacterium sp.* ASM-20A-77, ATCC 31090.

31. A method as claimed in claim 7, wherein the latter microorganism strain belongs to the species which includes *Corynebacterium sp.* ASM-20A-77, ATCC 31090.

32. A method as claimed in claim 8, wherein the latter microorganism strain belongs to the species which includes *Corynebacterium sp.* ASM-20A-77, ATCC 31090.

33. A method as claimed in claim 6, wherein the latter microorganism strain belongs to the species which includes *Corynebacterium sp.* ASM-T-13, ATCC 31089.

34. A method as claimed in claim 7, wherein the latter microorganism strain belongs to the species which includes *Corynebacterium sp.* ASM-T-13, ATCC 31089.

35. A method as claimed in claim 8, wherein the latter microorganism strain belongs to the species which includes *Corynebacterium sp.* ASM-T-13, ATCC 31089.

36. A method as claimed in claim 6, wherein the latter microorganism strain belongs to the species which includes *Corynebacterium sp.* ASM-K-106, ATCC 31088.

37. A method as claimed in claim 7, wherein the latter microorganism strain belongs to the species which includes *Corynebacterium sp.* ASM-K-106, ATCC 31088.

38. A method as claimed in claim 8, wherein the latter microorganism strain belongs to the species which includes *Corynebacterium sp.* ASM-K-106, ATCC 31088.

39. A method as claimed in claim 1, wherein at least one aqueous medium containing said viable cells is employed in the medium containing D-glucose in lieu of both or either one of said microorganism strains.

40. A method as claimed in claim 39, wherein said viable cells are derived from the microorganism strain which belongs to the species including *Acetobacter melanogenum* IFO 3293.

41. A method as claimed in claim 39, wherein said viable cells are derived from the microorganism strain which belongs to the species including *Acetomonas albosesamae* ATCC 21998.

42. A method as claimed in claim 39, wherein said viable cells are derived from the microorganism strain which belongs to the species including *Gluconobacter rubiginosus* IFO 3244.

43. A method as claimed in claim 39, wherein said viable cells are derived from the microorganism strain which belongs to the species including *Brevibacterium ketosoreductum* ASM-1005, ATCC 21914.

44. A method as claimed in claim 39, wherein said viable cells are derived from the microorganism strain which belongs to the species including *Brevibacterium sp.* ASM-856-4, ATCC 31083.

45. A method as claimed in claim 39, wherein said viable cells are derived from the microorganism strain which belongs to the species including *Brevibacterium sp.* ASM-3356-31, ATCC 31082.

46. A method as claimed in claim 39, wherein said viable cells are derived from the microorganism strain which belongs to the species including *Brevibacterium testaceum* IFO 12675.

47. A method as claimed in claim 39, wherein said viable cells are derived from the microorganism strain which belongs to the species including *Corynebacterium sp.* ASM-3311-6, ATCC 31081.

48. A method as claimed in claim 39, wherein said viable cells are derived from the microorganism strain which belongs to the species including *Corynebacterium sp.* ASM-20A-77, ATCC 31090.

49. A method as claimed in claim 39, wherein said viable cells are derived from the microorganism strain which belongs to the species including *Corynebacterium sp.* ASM-T-13, ATCC 31089.

50. A method as claimed in claim 39, wherein said viable cells are derived from the microorganism strain which belongs to the species including *Corynebacterium sp.* ASM-K-106, ATCC 31088.

* * * * *